United States Patent [19]

Fogarty et al.

[11] 4,271,839
[45] Jun. 9, 1981

[54] DILATION CATHETER METHOD AND APPARATUS

[75] Inventors: Thomas J. Fogarty, 770 Welch Rd., Palo Alto, Calif. 94304; Albert K. Chin, Stanford, Calif.

[73] Assignee: Thomas J. Fogarty, Palo Alto, Calif.

[21] Appl. No.: 60,408

[22] Filed: Jul. 25, 1979

[51] Int. Cl.³ ........................................ A61M 29/02
[52] U.S. Cl. .............................. 128/344; 128/349 B
[58] Field of Search .................. 128/262, 348, 349 B, 128/344, 325

[56] References Cited

U.S. PATENT DOCUMENTS

| | | | |
|---|---|---|---|
| 805,851 | 11/1905 | Goldfarb | 128/262 |
| 3,168,092 | 2/1965 | Silverman | 128/262 |
| 3,435,826 | 4/1969 | Fogarty | 128/348 |
| 3,467,101 | 9/1969 | Fogarty et al. | 128/348 |
| 3,467,102 | 9/1969 | Fogarty et al. | 128/348 |
| 3,525,329 | 8/1970 | Zeimer et al. | 128/262 |
| 3,583,391 | 6/1971 | Cox et al. | 128/262 |
| 3,866,599 | 2/1975 | Johnson | 128/6 |
| 3,896,815 | 7/1975 | Fehel et al. | 128/349 B |
| 3,911,927 | 10/1975 | Rich et al. | 128/262 |
| 3,923,065 | 12/1975 | Nozick et al. | 128/348 |
| 4,077,610 | 3/1978 | Masuda | 128/348 |
| 4,109,659 | 8/1978 | Sheridan | 128/262 |
| 4,195,637 | 4/1980 | Grüntzig et al. | 128/349 B |

FOREIGN PATENT DOCUMENTS 512456  11/1980  United Kingdom ................. 128/344

*Primary Examiner*—Hiram Bernstein
*Attorney, Agent, or Firm*—Naylor, Neal & Uilkema

[57] ABSTRACT

A balloon catheter wherein the balloon is inverted within the distal end of the catheter for eversion therefrom and extrusion through a partially occluded blood vessel in response to the exertion of internal fluid pressure on the balloon. The catheter is designed to extrude through the occluded vessel in advance of substantial lateral expansion and, upon full extension, is adapted to expand to a condition at least partially dilating the occlusion. A cord connected to the balloon and extending through the catheter provides means whereby tension may be applied to the balloon to reinvert it within the catheter. A reservoir in communication with the inner lumen of the catheter provides a closed fluid-filled system whereby the balloon may be sequentially everted and reinverted without venting outside of the system.

14 Claims, 10 Drawing Figures

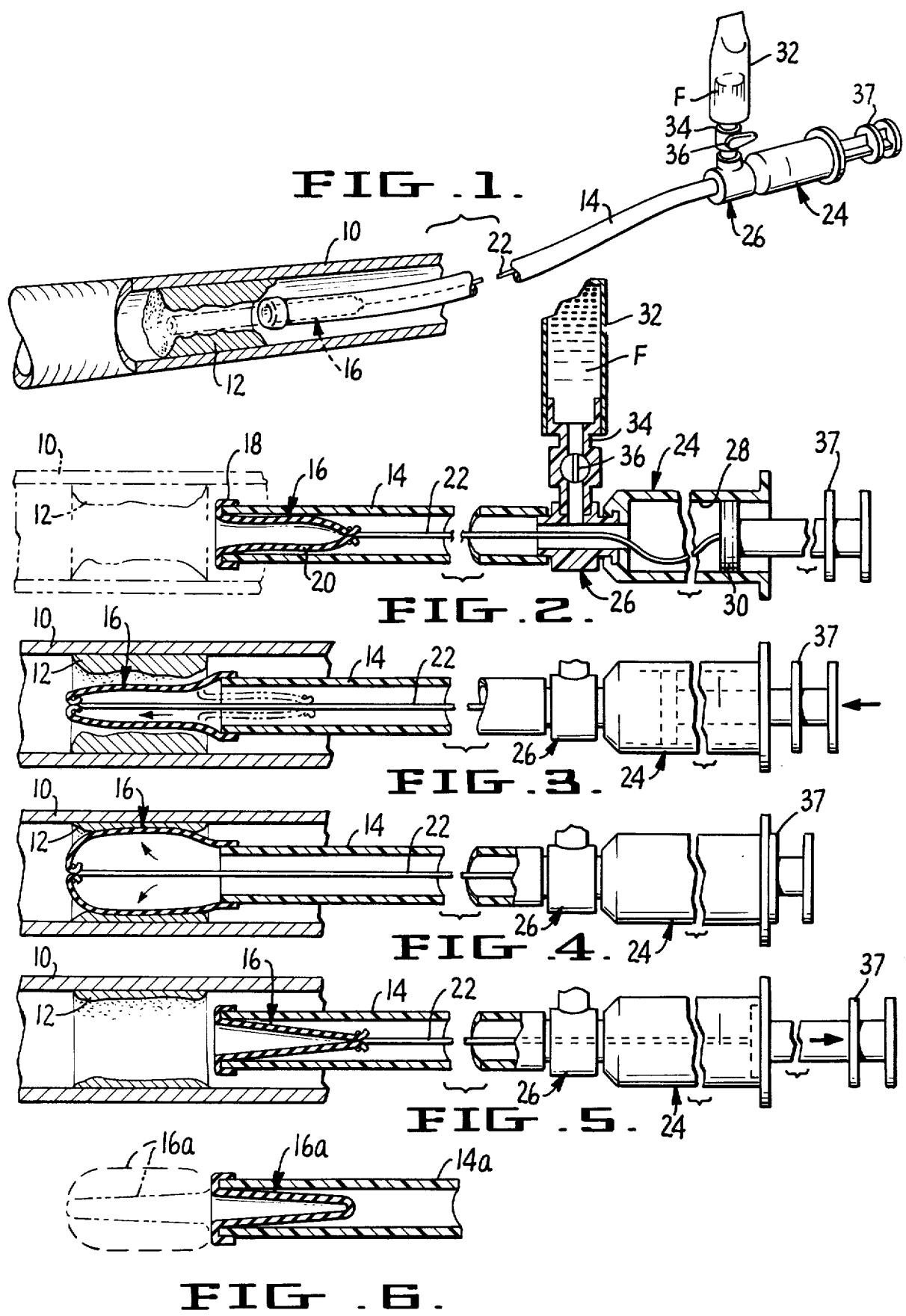

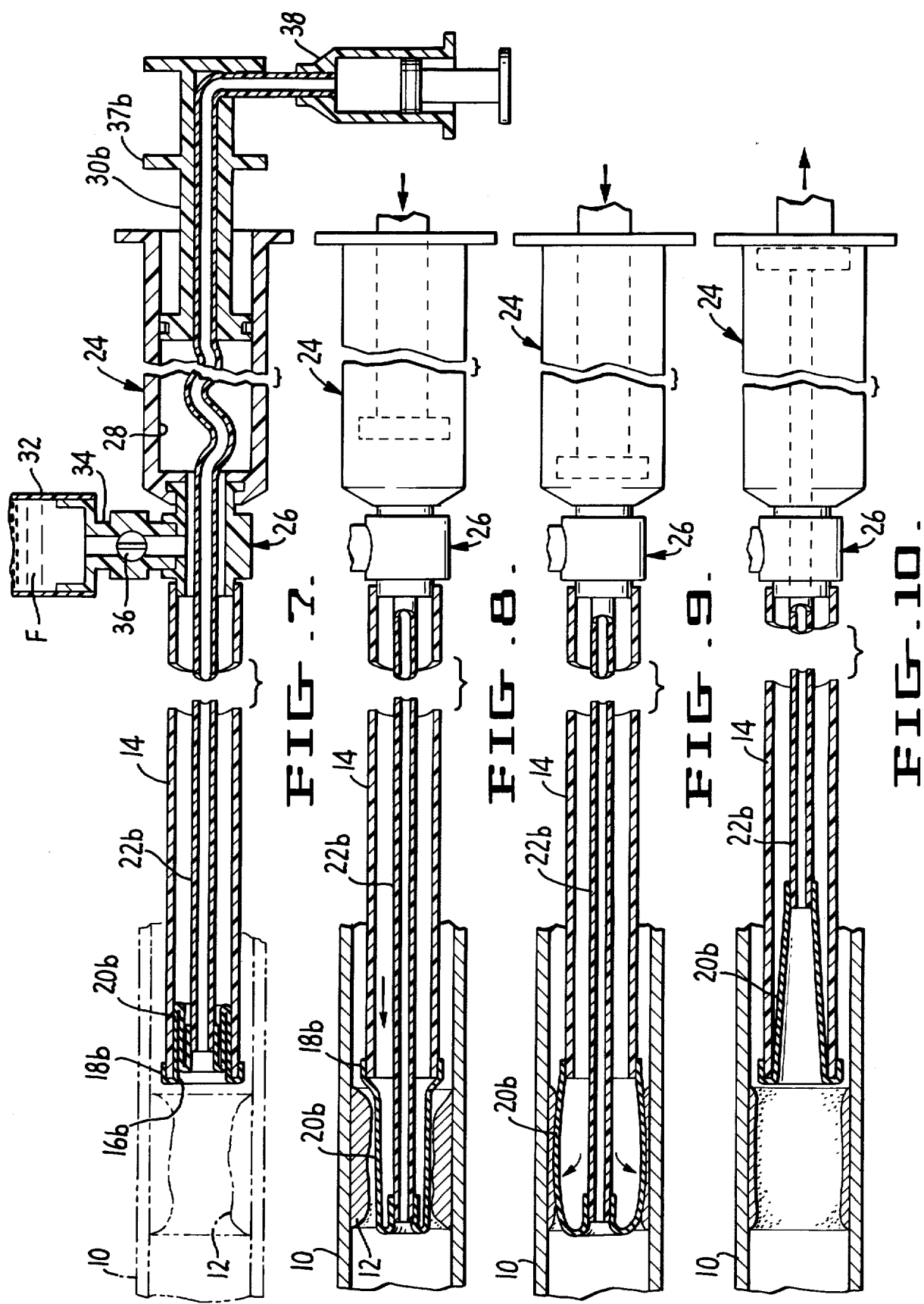

DILATION CATHETER METHOD AND APPARATUS

BACKGROUND OF THE INVENTION

The present invention relates to a method and apparatus for use in dilating occluded blood vessels. The invention is particularly concerned with such a method and apparatus wherein dilatation is achieved through means of a balloon element which is initially inverted within the distal end of a catheter and, in use, extruded through and expanded within the occlusion being treated. The invention is intended for use in treating either arterial or venous occlusions.

Prior art efforts for the treatment of occluded blood vessels have relied primarily upon the employment of bypass vessels or some surgical technique whereby the occlusion is physically removed from the vessel being treated. Another recent technique for treating occluded vessels relies upon the insertion of some type of an instrument into the vessel to dilate the occlusion through a stretching or compressing process. The present invention is concerned with a technique of the latter type.

A principal problem with the employment of techniques wherein instruments are inserted into the vessel to effect dilatation by compression or stretching is that the instruments may damage the vessel and/or dislodge material therefrom. Another problem with such techniques is that it has been very difficult to place the instruments used therefor in highly occluded or small diameter vessels. These problems have resulted primarily from the construction and size of the instruments. In one such technique, the instruments take the form of progressively larger catheters which are successively forced through the vessel being treated. In another technique, the instruments have taken the form of an inflatable catheter which is forced into place within the occluded area to be treated and, once in place, inflated. These prior catheters, although flexible, are necessarily somewhat hard and inelastic, in order to enable the catheter to be advanced large distances through the arterial or venous systems. The inherent hardness of these catheters contribute to the problems of vessel damage and material dislodgement mentioned previously.

SUMMARY OF THE INVENTION

The present invention relies on an apparatus and method wherein a highly flexible balloon is inverted within the distal end of a flexible catheter and everted from the catheter for extrusion through the occluded section of the vessel to be treated. The balloon and catheter are so designed that the balloon may symmetrically evert from the catheter and extrude through the occlusion in anisotropic fashion in advance of substantial lateral expansion of the balloon. Eversion of the balloon from the catheter is effected through means of the application of internal fluid pressure to the catheter. Once the balloon is in place within the occluded section of the vessel, continued fluid pressure is applied to laterally expand the balloon and dilate the occlusion. The process of laterally expanding the balloon to dilate the occlusion may be pulsed by repeatedly increasing and decreasing the fluid pressure within the catheter. In the preferred embodiments, a cord element extends through the catheter and is connected to the balloon to reinvert the balloon within the catheter after treatment of the occlusion is complete.

A principal object of the invention is to provide an inflatable catheter for use in dilating arterial or venous occlusions without injury to the vessel being treated or dislodgment of material therefrom.

Another object is to provide an inflatable catheter for use in dilating arterial or venous occlusions, such that a soft, inflatable dilating portion is advanced through the occluded area in a gentle manner, with no need to force a hard catheter through the occluded area prior to dilatation.

Another and more specific object is to provide such a catheter wherein the inflatable element is initially inverted within the end of the catheter and, upon being placed in close proximity to the occlusion to be treated, everted for extrusion through the occlusion in advance of substantial lateral expansion.

Still another object of the invention is to provide such a catheter wherein the inflatable element is evertable from the catheter in a symmetrical fashion.

Yet another object of the invention is to provide such a catheter wherein a mechanism is contained within the catheter for reinverting the inflatable element after its expansion for dilatation purposes.

Another object related to the latter object is to provide such a mechanism which assures that the inflatable element, or fragments thereof, cannot separate from the catheter.

Another object is to provide such a catheter wherein the reinversion mechanism includes a secondary catheter extending through the primary catheter and the inflatable element to enable the taking of pressure measurements or the making of injections without removal of the catheter from the vessel being treated.

A further object of the invention is to provide an inflatable catheter which enables the dilatation of select limited areas of the vessel being treated.

A further specific object of the invention is to provide an inflatable dilatation catheter wherein the catheter body may be of a diameter less than the lumen of the vessel being treated and the inflatable element is initially inverted within the distal end of the catheter.

A further object of the invention is to provide an inflatable dilatation catheter which may be extruded into place within an occluded section of the vessel being treated without materially disturbing the occlusion and, once in place, may be repeatedly laterally expanded and contracted to subject the occlusion to pulsing dilatation.

The foregoing and other objects will become more apparent when viewed in light of the following detailed description and accompanying drawings.

BRIEF DESCRIPTION OF THE DRAWINGS

FIG. 1 is a perspective view illustrating an occluded vessel in the process of being treated by a first embodiment of the invention, with parts of the vessel broken away and shown in section;

FIG. 2 is an elevational cross-sectional view illustrating the catheter of the first embodiment and a phantom line representation of a vessel to be treated, as the catheter would appear when being directed to an occluded section of the vessel;

FIG. 3 is a cross-sectional elevational view similar to FIG. 2, illustrating the first embodiment catheter in association with a vessel being treated, as the inflatable element appears when first extruded through the occluded section of the vessel;

FIG. 4 is a cross-sectional elevational view, similar to FIG. 3, illustrating the inflatable element, after it has expanded to dilate the occlusion being treated;

FIG. 5 is a cross-sectional elevational view, similar to FIG. 4, illustrating the inflatable element after completion of the dilatation treatment and reinversion of the element into the catheter;

FIG. 6 is a cross-sectional elevational view of a second embodiment of the catheter with solid lines showing the inflatable element in the inverted condition and phantom lines showing the inflatable element in progressive stages of eversion and lateral expansion;

FIG. 7 is a cross-sectional elevational view illustrating the catheter of a third embodiment of the invention and a phantom line representation of a vessel to be treated, as the catheter would appear when being directed to the occluded section of the vessel;

FIG. 8 is a cross-sectional view, similar to FIG. 7, illustrating the third embodiment catheter in association with a vessel being treated, as the inflatable element appears when first extended through the occluded section of the vessel;

FIG. 9 is a cross-sectional elevational view, similar to FIG. 8, illustrating the third embodiment inflatable element after it has expanded to dilate the occlusion being treated; and FIG. 10 is a cross-sectional elevational view, similar to FIG. 9, illustrating the third embodiment inflatable element after completion of the dilatation treatment and reinversion of the element into the catheter.

DESCRIPTION OF THE FIRST EMBODIMENT

FIG. 1 illustrates a blood vessel 10 partially occluded by an occlusion 12. As shown, the vessel takes the form of an artery and the occlusion is what is commonly known as an arteriosclerotic plaque or atheroma. This is the type of adhering occlusion with which the inventive apparatus and method is expected to find primary application. It should be understood, however, that the invention is applicable in treating other types of occluded vessels wherein dilatation is desired. For example, the invention may be used in treating occlusions resulting from fibromuscular-dysplasia in veins.

The principal elements of the first embodiment apparatus shown in FIG. 1 comprise: a flexible generally inelastic catheter 14 fabricated of an inert polymer material such as Dacron; a balloon element 16 fabricated of a highly elastic resilient material, such as latex, said element having a mouth portion (attachment shoulder) 18 peripherally secured to the distal end of the catheter 14 and a body portion 20 initially inverted within the catheter; a cord 22 extending through the catheter 14 and connected at one end of the body portion 20 of the balloon element; a syringe 24 connected to the proximate end of the catheter 14 through an intermediate tubular coupling 26, said syringe having a cylinder 28 with a positive displacement piston plunger 30 sealingly and slidably received therein, which plunger has the proximate end of the cord 22 connected thereto; a flexible reservoir 32 removably connected in fluid communication with the interior of the coupling 26 through means of a tubular lateral extension 34 formed as part of the coupling; and a selectively operable shut-off valve 36 interposed in the extension 34. The catheter may vary in length, depending upon the application in which it is intended to be used, and commonly measures up to 30 inches in length. Cross-sectional dimensions of the catheter may vary, depending upon the application, and are generally chosen so that the outside diameter of the catheter is equal to about one-half the inner diameter of the nonoccluded lumen of the vessel being treated. In one typical embodiment, the catheter and associated balloon element have the following dimensions:

| Catheter Body Dimensions | |
| --- | --- |
| O.D.: | .085 inches |
| I.D.: | .060 inches |
| Length: | Variable up to about 30 inches |

| Balloon Element Dimensions When Detached from Catheter | |
| --- | --- |
| Reduced Diameter Body O.D.: | .034 inches |
| Reduced Diameter Body I.D.: | .020 inches |
| Reduced Diameter Body Thickness: | .007 inches |
| Attachment Shoulder O.D.: | .14 inches |
| Attachment Shoulder Thickness: | .007 inches |
| Attachment Shoulder Length: | .26 inches |

| Attached Balloon Dimensions | |
| --- | --- |
| Uninflated Inverted Length: | .20 inches |
| Inflated Length After Eversion: | .70 inches |
| Inflated O.D.: | .16 inches |

In the preferred embodiment, the length, wall thickness, and O.D. of the balloon element are such that the element does not drag on the inner walls of the catheter when the element is everted out of the catheter symmetrically. The balloon element should ideally have a length no more than about 25 times the I.D. of the catheter.

The material and relative thicknesses of the balloon element are chosen so that expansion of the balloon element out of the end of the catheter takes place in anisotropic fashion with the element first everting out of the catheter in advance of substantial lateral expansion and then, after eversion, laterally expanding in response to the continued exertion of fluid pressure internally of the catheter. Once everted out of the catheter, the balloon element is designed to laterally expand to an outside diameter equal to or greater than the I.D. of the nonoccluded vessel treated. Although such characteristics may be achieved through the employment of an elastomeric balloon element such as that of the foregoing example, it is anticipated that similar characteristics may be achieved by fabricating the balloon element of a folded generally inelastic flexible material, such as polyvinyl chloride, which is adapted to first evert to an extended condition and then unfold to a laterally expanded condition.

The cord 22 should be flexible and generally inelastic and of such a length that it will not restrict eversion of the balloon element 16 as it is moved from the inverted condition shown in FIG. 2 to the extended condition shown in FIG. 3. To permit such unrestricted extension of the balloon element, the cord is ideally provided with a slack portion, as shown in the cylinder 28 illustrated in FIG. 2. The cord should also, however, be of such a length that retraction of the plunger 30 beyond a predetermined limit functions to reinvert the balloon element within the distal end of the catheter, as shown in FIG. 5.

The catheter 14, syringe 24 and reservoir 32 contain an incompressible fluid F. Preferably, this fluid is radiopaque in order to facilitate the radiographic monitoring of the position of the catheter and progress of the dilatation procedure. The valve 36 provides means whereby this fluid may be selectively captured between the balloon element 16 and the piston 30 (i.e., when the valve is closed) or permitted to charge into and out of the reservoir 32 (i.e., when the valve 36 is open). In either condition, however, the reservoir 32 assures that the catheter 14 is always filled with fluid. Prior to the dilatation procedure, both the catheter and the reservoir are purged of air and filled with fluid. The reservoir is detached from the catheter, both portions are separately filled, and the reservoir and catheter are reattached. With the valve in the open condition, as it would be in the FIG. 4 condition, the piston plunger 30 may be retracted to tension the cord 22 and, thus, draw the balloon element 16 into the reinverted condition within the catheter. With the valve 36 closed, the piston plunger 30 may be compressed to subject the catheter 14 to internal pressure and, thus, evert the balloon element out of the end of the catheter, as shown in FIG. 3. In the preferred mode of operation, the piston plunger 30 is depressed to a predetermined degree prior to closing of the valve 36 to provide for carefully controlled expansion of the balloon element by depression of the plunger and assure that the cord 22 is slack throughout eversion of the balloon element out of the catheter. Suitable indicia may be provided on the syringe 24 to index the point of plunger travel at which the valve 36 should be closed. The preferred construction also includes a shoulder 37 on the plunger 30 for abutment with the end of the cylinder 28 to limit inward movement of the plunger.

In using the first embodiment catheter to practice the method of the present invention, an incision is first made in the vessel to one side of the occlusion to be treated and then the distal end of the catheter 14 is introduced into the vessel through the incision. The catheter is then fed through the vessel to position the distal end thereof proximate one end of the occlusion, as shown in FIGS. 1 and 2. At or prior to this time, the position of the plunger 30 is adjusted and the valve 36 is closed. With the catheter so positioned and the plunger so conditioned, the next step is to apply pressure to the plunger, as shown in FIG. 3, to subject the catheter to internal fluid pressure and evert the body portion of the balloon element therefrom for extrusion through the occlusion 12. In the preferred mode, during such eversion, the balloon element extends axially without substantial lateral expansion. Once the balloon element has extruded through the occlusion 12, the application of continued fluid to the catheter through the plunger 30 functions to laterally expand the balloon element as shown in FIG. 4 and, thus, dilate the occlusion. Such expansion and dilatation may be pulsed by moving the plunger 30 in and out. Throughout the placement and dilatation process, the progress of the treatment may be radiographically monitored. The extent of stretching during the dilatation process as a result of lateral expansion of the balloon may vary somewhat, depending upon the circumstances involved. Ideally, the balloon is expanded so as to have an outside diameter equal to or slightly greater then the internal diameter of the nonoccluded vessel.

Once the dilatation is complete, the valve 36 is opened and the plunger 30 is retracted, as shown in FIG. 5, to tension the cord 22 and, thus, reinvert the balloon element within the catheter. At this point, the catheter may be removed from the vessel, and the incision through which the catheter was introduced may be closed. It is also possible, depending upon the circumstances involved, that the catheter may be moved into a further section of the occlusion being treated, or on to a successive occlusion prior to removal of the catheter. In such a case, the balloon element would be everted and re-expanded, as shown in FIGS. 2, 3 and 4 for each successive dilatation treatment and, ultimately, the balloon element would be reinverted and the catheter removed from the vessel.

DESCRIPTION OF THE SECOND EMBODIMENT

The embodiment of FIG. 6 corresponds to that of the first embodiment, with the exception that the balloon element, designated 16a, is not provided with a cord to draw it back into the reinverted condition within the catheter, designated 14a. Other than this difference, the structure and mode of operation of the embodiment shown in FIG. 6 would be identical to that of the first embodiment described in the foregoing discussion with respect to FIGS. 1 to 5. With the FIG. 6 embodiment, reinversion is achieved through means of the vacuum created within the catheter 14a by retraction of the plunger of the syringe (not illustrated) associated with the catheter 14a. It is also possible that the FIG. 6 balloon element might be permitted to remain in the extended, but uninflated, condition during the course of removal of the catheter 14a after a dilatation treatment. Once the catheter 14a is removed from the vessel being treated, external means could be used to assist in reinversion of the balloon element.

DESCRIPTION OF THE THIRD EMBODIMENT

The principal difference between the third embodiment, illustrated in FIGS. 7 to 10, and the first embodiment described in the foregoing discussion with respect to FIGS. 1 to 5 is that the third embodiment employs an annular balloon element 16b in place of the closed bulbous element 16, and a tubular cord element in the form of a flexible catheter 22b in place of the simple cord 22. The purpose of these differences is to provide a passage (i.e., the passage through the catheter 22b and the annular balloon element 16b) through which pressure within the vessel being treated may be measured, or injections into the vessel may be made. For the latter purpose, the plunger 30b (see FIG. 7) is provided with a passage through which the catheter 22b extends and a syringe 38 is connected to the proximate end of the catheter 22b.

The vessel and occlusion depicted in FIGS. 7 to 10 correspond to those of FIGS. 1 to 5 and, accordingly, are designated by the numerals 10 and 12, respectively. The elements of the third embodiment catheter and inflating mechanism which correspond to those of the first embodiment are designated in FIGS. 7 to 10 by numerals corresponding to those used in FIGS. 1 to 5, as follows: catheter 14; syringe 24; tubular coupling 26; cylinder 28; flexible reservoir 32; tubular lateral extension 34; and, shut-off valve 36.

The mouth portion (attachment shoulder) of the element 16b is designated 18b and the body portion of the element 16b is designated 20b. In the preferred construction, the balloon element 16b is fabricated of latex. The inner catheter 22b to which the balloon element 16b is connected may be fabricated of any suitable material, such as Dacron or polyvinyl chloride. Ideally, the material from which the catheter 22b is fabricated is flexible and generally inelastic.

Like the balloon element 16, the annular balloon element 16b is fabricated so that it may evert out of the end of the catheter 14 in anisotropic fashion, with the balloon element first everting out of the catheter in advance of substantial lateral expansion and then, upon eversion, being laterally expansible in response to the continued exertion of fluid pressure internally of the catheter 14. The catheter 22b serves a function similar to the cord 22 and should be flexible and generally inelastic and of such a length that it will not restrict eversion of the balloon element 16b out of the catheter 14. To permit such unrestricted extension of the element 16b, the catheter 22b is ideally provided with a slack portion, as shown in the cylinder 28 in FIG. 7. The catheter 22b should also, however, be of such a length that retraction of the plunger 30b beyond a predetermined limit functions to reinvert the element 16b within the distal end of the catheter 14, as shown in FIG. 10.

The third embodiment catheter 14, syringe 24 and reservoir 32 contain an incompressible fluid F and operate, in cooperation with the valve 36, in the same manner described in the foregoing discussion with respect to the first embodiment. A stop shoulder 37b, corresponding to the aforedescribed shoulder 37, is provided on the plunger 30b to limit inward movement of the plunger relative to the cylinder 28.

The third embodiment catheter is used to practice the method of the invention in essentially the same manner described in the foregoing discussion with respect to the first embodiment. During this use, an incision is first made in the vessel to one side of the occlusion to be treated and then the distal end of the catheter 14 is introduced into the vessel through the incision. The catheter is then advanced through the vessel to a position proximate one end of the occlusion and, once so positioned, the plunger 30b is used to first evert the element 16b out of the catheter 14 and through the occlusion and then to expand the element 16b laterally to dilate the occlusion. As in the first embodiment catheter, the element 16b is extruded through the occlusion in advance of substantial lateral expansion of the element. Expansion of the element for dilatation purposes may be pulsed by moving the plunger 30b in and out and the progress of dilatation may be radiographically monitored. The extent of stretching during the dilatation process may vary somewhat, depending upon the circumstances involved. Generally, the element 16b is expanded so as to have an outside diameter equal to or slightly greater than the internal diameter of the nonoccluded section of the vessel being treated.

FIGS. 7, 8, 9 and 10 show the successive steps in practicing the invention. In FIG. 7, the catheter is shown as it would appear when being directed to the situs of the occlusion. FIG. 8 shows the catheter as it would appear when the element 16b is initially expanded for extrusion through the occlusion. From this figure, it will be seen that the catheter 22b is drawn through the occlusion with the element 16b and, thus, provides a passage through the element 16b. FIG. 9 shows the element 16b as it would appear when inflated to dilate the occlusion 12. In FIG. 10, the catheter is shown in the condition it would assume when the valve 36 is opened and the plunger 30b is retracted to tension the catheter 22b and, thus, reinvert the element 16b within the catheter 14. With the element 16b so reinverted, the catheter may be moved to another situs within the vessel for further dilatation treatment, or removed from the vessel.

The lumen of the catheter 22b provides means whereby injections or pressure measurement can be made while the third embodiment catheter 14 is in place in a vessel. Such injections or measurements can be made at any time as the lumen of the catheter 22b remains open at all times.

CONCLUSION

Although preferred embodiments of the invention have been illustrated and described, it should be understood that the invention is not intended to be limited to the specifics of these embodiments, but rather is defined by the accompanying claims.

What is claimed is:

1. Apparatus for dilating a partially occluded section of a blood vessel, said apparatus comprising: an elongated flexible generally inelastic catheter having an outside diameter less than the internal diameter of the nonoccluded vessel; balloon means inverted within the catheter, said balloon means having a mouth peripherally sealed to the distal end of the catheter and being evertable out of the catheter in response to the exertion of fluid pressure within the catheter for substantially anisotropic expansion out of the catheter and through the occluded section of the vessel in advance of substantial lateral expansion and, upon eversion out of the catheter, being laterally expansible in response to the continued exertion of fluid pressure internally of the catheter to an outside diameter equal to or greater than the internal diameter of the vessel; and means to selectively impart internal pressure to the catheter.

2. An apparatus according to claim 1 wherein the balloon means comprises a bag having an outside diameter wall thickness and length such that the bag does not drag on the inner walls of the catheter when everted out of the catheter symmetrically.

3. An apparatus according to claim 2, wherein the catheter has an outside diameter approximately equal to one-half the internal diameter of the nonoccluded vessel.

4. An apparatus according to claim 1 wherein the balloon means, when in the inverted condition within the catheter, has a length no more than twenty-five times the internal diameter of the catheter.

5. An apparatus according to claim 1 further compising cord means extending through the catheter and connected to the balloon means, said cord means having a length greater than that of the catheter whereby the balloon may be fully everted out of the catheter without resistance by said cord means and, upon release of internal fluid pressure from the catheter, being tensionable to reinvert the balloon means within the catheter; and means to selectively apply tension to the cord means.

6. An apparatus according to claim 5 wherein: the cord means comprises a flexible catheter; and, the balloon means comprises an annular elastomeric member having the inner periphery thereof sealingly secured to the cord means catheter and the outer periphery thereof sealingly secured to the catheter within which the balloon means is inverted.

7. A method for dilating an occlusion within a blood vessel, said method comprising: providing a flexible catheter having a balloon with the mouth thereof peripherally sealed to the distal end of the catheter and the body thereof inverted within the catheter; introducing said catheter into the vessel so as to position the distal end thereof proximate one end of the occlusion; applying internal fluid pressure to the catheter so as to evert the body of the balloon out of the catheter and extrude said body through at least a portion of the occlusion; and applying continued internal pressure to the catheter to expand the balloon to an outside sufficient to at least partially dilate the occlusion.

8. A method according to claim 7, further comprising: reinverting to balloon within the catheter and withdrawing the catheter from the vessel.

9. A method according to claim 7, further comprising: extending a cord through the catheter and connecting one end of the cord to the end of the balloon so that the cord is normally slack and does not restrict eversion or expansion of the balloon; releasing the fluid pressure on said catheter after expansion of the balloon to an outside diameter equal to or greater than the nonoccluded inner diameter of the vessel; and, after so releasing the internal pressure on the catheter, applying tension to the cord to reinvert the balloon within the catheter.

10. A method according to claim 7 wherein the balloon when everted within the catheter, has an outside diameter less than the internal diameter of the catheter and length no greater than twenty-five times the internal diameter of the catheter.

11. Apparatus for dilating a partially occluded section of a blood vessel, said apparatus comprising an elongated flexible catheter adapted for passage through the vessel; balloon means inverted within the catheter, said balloon means having a mouth peripherally sealed to the distal end of the catheter and being evertable out of the catheter in response to the exertion of fluid pressure within the catheter for eversion out of the catheter and extrusion through the occluded section of the vessel in advance of substantial lateral expansion and, upon eversion out of catheter, being laterally expansible in response to continued exertion of fluid pressure internally of the catheter to an outside diameter sufficiently large to at least partially dilate the occlusion; and means to selectively impart internal pressure to the catheter.

12. An apparatus according to claim 11 wherein the means to selectively impart internal pressure to the catheter comprises a syringe connected to the proximal end of the catheter, said syringe having a piston moveable in a first direction for displacing fluid into the catheter and a second direction for displacing fluid out of the catheter; and wherein said apparatus further comprises cord means extending through the catheter and connected between the balloon and piston to permit unrestricted eversion and expansion of the balloon means in response to movement of the piston in the first direction and to exert reinverting tension force on the balloon in response to movement of the piston beyond a predetermined limit in the second direction.

13. An apparatus according to claim 12 wherein: the cord means comprises a flexible catheter; and, the balloon means comprises an annular elastomeric member having the inner periphery sealingly secured to the cord means catheter and the outer periphery thereof sealingly secured to the catheter within which the balloon means is inverted.

14. An apparatus according to claim 12, further comprising: a reservoir interposed between the catheter and syringe; valve means to selectively open and close said reservoir to fluid communication with the catheter.

* * * * *